United States Patent [19]

Bodenmann et al.

[11] Patent Number: 4,893,721

[45] Date of Patent: Jan. 16, 1990

[54] TAMPER-PROOF CAPSULES

[75] Inventors: Hans U. Bodenmann, Muenchenstein, Switzerland; Steven A. Roberts, Greenwood, S.C.; Fritz Wittwer, Lupsingen, Switzerland

[73] Assignee: Warner-Lambert Company, Morris Plains, N.J.

[21] Appl. No.: 674,348

[22] Filed: Nov. 21, 1984

Related U.S. Application Data

[63] Continuation of Ser. No. 438,148, Oct. 29, 1987, abandoned.

[51] Int. Cl.$^4$ ........................ B65D 43/10; A61B 19/02

[52] U.S. Cl. .......................................... 220/8; 206/530

[58] Field of Search ............... 206/528, 530, 534, 525, 206/226, 539, 459, 807, 115; 220/306, 309, 352, 356, 327, 292, 291, 413

[56] References Cited

U.S. PATENT DOCUMENTS

| | | | |
|---|---|---|---|
| 666,723 | 1/1901 | Wilmot | 220/309 |
| 1,025,207 | 5/1912 | Sanford | 206/226 |
| 1,861,047 | 5/1932 | Colton | 206/807 |
| 3,258,115 | 6/1966 | Kath | 220/352 |
| 3,285,408 | 11/1966 | Carnaghi et al. | 220/8 |
| 3,664,495 | 5/1972 | Graham et al. | 220/8 |
| 3,702,657 | 11/1972 | Mottin et al. | 206/539 |
| 3,709,401 | 1/1973 | Walstrom | 220/327 |
| 3,823,843 | 7/1974 | Stephens et al. | 220/356 |
| 4,040,536 | 8/1977 | Schwarz | 220/8 |
| 4,106,622 | 8/1978 | Windischman | 206/459 |

OTHER PUBLICATIONS

*The Theory and Practice of Industrial Pharmacy,* Second Edition; Lachman, M.D. et al.

*Primary Examiner*—George E. Lowrance

*Attorney, Agent, or Firm*—Daniel A. Scola, Jr.; Howard Olevsky; Stephen Raines

[57] ABSTRACT

A hard shell tamper-proof capsule having cylindrical, telescopically joinable, coaxial cap and body parts each having a side wall, an open end and a closed end, the cap and body being adapted to be mutually joined; characterized in that the body closed end has either a generally hemispheroidal, a pyramidical, a conical or a flat outside surface, and that the body side wall is totally enclosed within the cap side wall thereby exposing only the outside surface of the body closed end for gripping, which impedes separation of and tampering with the joined capsule.

For additional security the tamper-proof capsule may be provided with locking means of circumferentially extending ridges or grooves.

For further security the tamper-proof capsule may be provided with sealing means such as hot water, steam, or hot solutions or emulsions.

4 Claims, 28 Drawing Sheets

TAMPER-PROOF CAPSULES

This is a continuation of co-pending application Ser. No. 438,148 filed on Oct. 29, 1982, now abandoned.

BACKGROUND OF THE INVENTION

1. Field of the Invention

The present invention relates to tamper-proof capsules, and particularly to hard shell pharmaceutical capsules having cylindrical, telescopically joinable, coaxial cap and body parts.

2. Description of the Prior Art

The need for tamper-proof capsules stems from the determination that hard shell gelatin capsules containing medicaments are susceptible to tampering by separating the cap and body parts, modifying or adding to the medicaments therein, and rejoining the body and capsule parts. The prior art of U.S. Pat. No. 1,861,047 has utilized a circular band of hardened gelatin covering the seam between the body and cap part which indicates when the capsule parts have been separated. This procedure is deficient in that tamperers can easily separate the body part from the cap part, modify or add to the medicaments therein, rejoin the capsule and body parts, and reband the rejoined capsule so as to avoid detection of tampering.

A need therefore exists to provide a simple and effective tamper-proof capsule.

SUMMARY OF THE INVENTION

In accordance with the present invention, a tamper-proof capsule is disclosed, which comprises a hard shell capsule having cylindrical, telescopically joinable, coaxial cap and body parts each having a side wall, an open end and a closed end, the cap and body being adapted to be mutually joined; characterized in that the body closed end has either a generally hemispheroidal, a pyramidical, a conical or a flat outside surface; and the body side wall is totally enclosed within the cap side wall thereby exposing only the outside surface of the body closed end for gripping, which impedes separation of and tampering with the joined capsule.

The tamper-proof capsule may further include locking means of one or more circumferentially extending ridges or grooves.

The tamper-proof capsule of the present invention may further include venting means to permit air to escape from within the capsule when joined.

The tamper-proof capsule of the present invention may also include pre-locking position means to assure the partial joining of the capsule part in a constant predetermined length prior to filling and final joining.

The tamper-proof capsule of the present invention may also include a reduction of the diameter of the free edge of the capsule body in order to avoid an abutment when the capsule body is telescoped within the capsule cap.

The tamper-proof capsule of the present invention may further include additional binding by the application of sealing means such as hot water, steam, heat or hot solutions or emulsions.

In operation, the hard shell capsule coaxial cap and body parts are telescopically joined and the cap side wall completely encloses the body side wall so that only the body closed end is exposed and presents a minimal surface for gripping and withdrawal of the body part from within the cap, thereby impeding separation of the capsule for the purpose of tampering. Additional locking means and sealing means are provided in order to further impede the withdrawal of the body part from within the cap, thereby making it even more difficult to separate the body part from the cap part for the purpose of tampering.

Accordingly, it is a principal object of the present invention to provide a hard shell tamper-proof capsule having cylindrical, telescopically joinable, coaxial cap and body parts.

Other objects and advantages will become apparent to those skilled in the art from a consideration of the detailed description which proceeds with reference to the following illustrative drawings.

It is to be understood that the circumferentially extending ridge of this and all of the following embodiments of the present invention also includes a segmented or discontinuous ridge so that spaces between the ridge act as vents to permit air to escape from within the capsule when joined.

Figure 1:
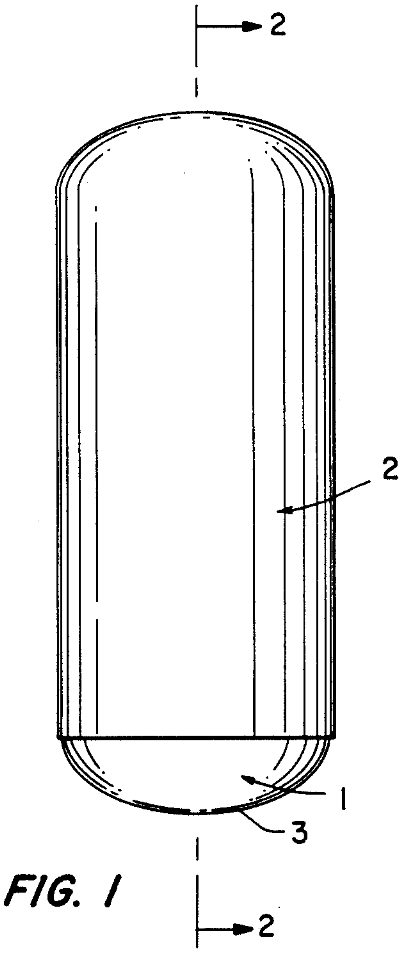
FIG. 1 is a top plan view of a first embodiment of the present invention. The body part 1 is inserted within the cap part 2 so that the hemispheroidal closed end 3 of the body part 1 presents a minimal exposed outside closed end surface for gripping and withdrawal of the body part 1 from within the cap part 2.
Figure 2:
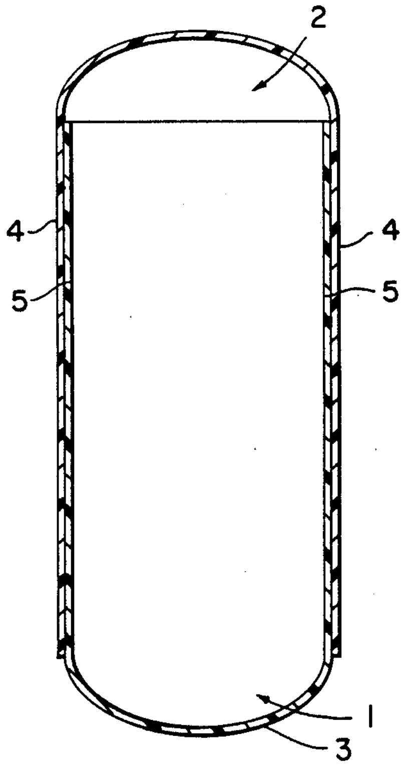
FIG. 2 is a side sectional view of FIG. 1 along line 2—2 showing the continuous and total overlap of cap side wall 4 over body side wall 5.
Figure 3:
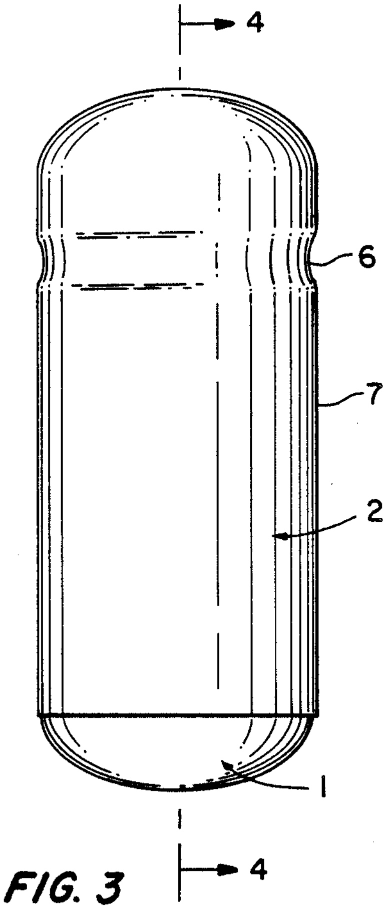
FIG. 3 is a top plan view of a second embodiment of the present invention wherein the cap part has a locking means of a circumferentially extending ridge 6 extending inwardly from the inner side wall surface 7 of the cap part 2.
Figure 4:
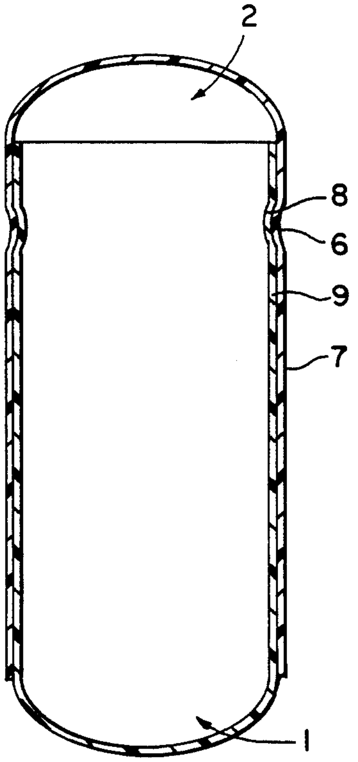

FIG. 4 is a side sectional view of FIG. 3 along line 4—4 showing the locking means by mating of the ridge 6 of the inner surface 7 of the cap part 2 with a groove 8 on the outer side wall surface 9 of the body part 1, when the capsule has been telescopically joined.

It is to be understood that the circumferentially extending ridge of the cap part mating with the groove of the body part of this and all of the following embodiments of the present invention are interchangeable with a circumferentially extending groove of the cap part mating with a ridge of the body part.

Figure 5:
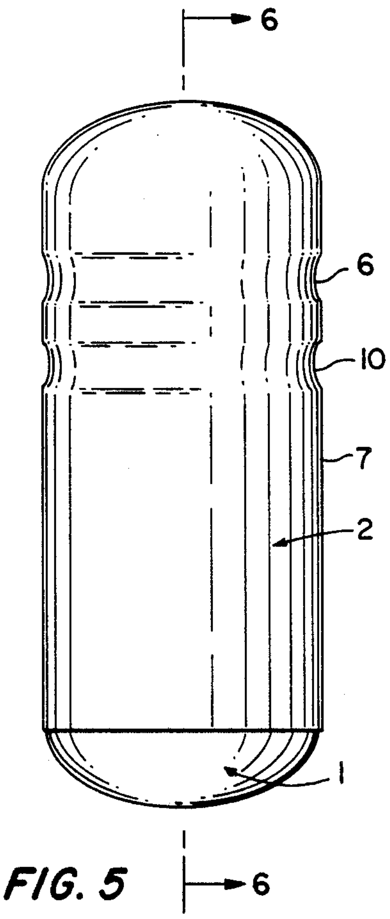

FIG. 5 is a top plan view of a third embodiment of the present invention wherein the cap part has a locking means of two circumferential ridges 6, 10 extending inwardly from the inner side wall surface 7 of the cap part 2.

Figure 6:
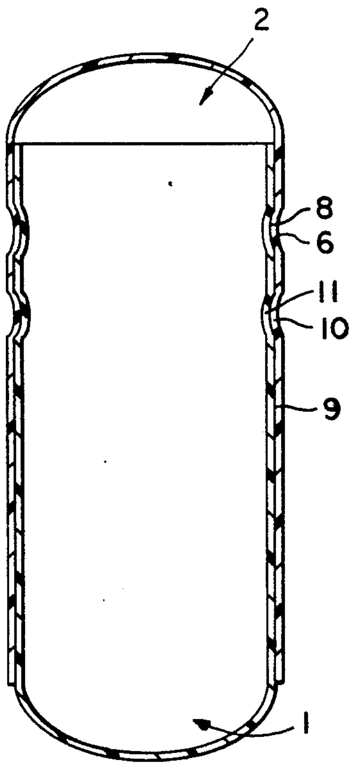

FIG. 6 is a side sectional view of FIG. 5 along line 6—6 showing the locking means by mating of the inwardly extending ridges, 6, 10 of the cap part 2 with two circumferential extending grooves 8, 11 extending inwardly from the side wall outer surface 9 of body part 1.

Figure 7:
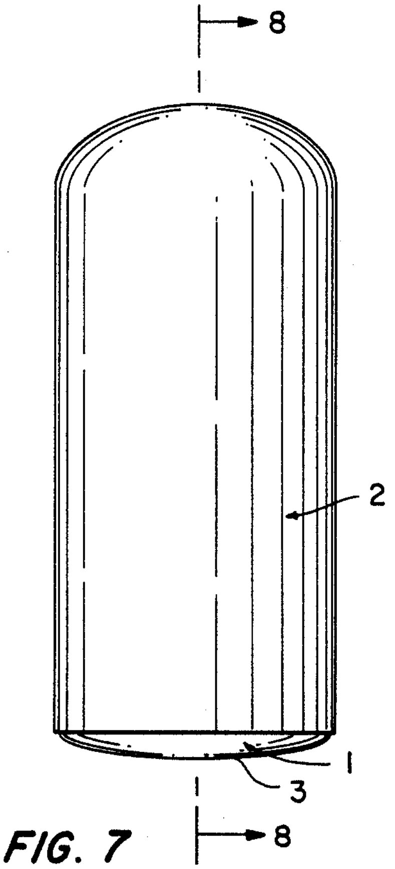

FIG. 7 is a top plan view of a fourth embodiment of the present invention showing the body part 1 telescoped within the cap part 2 so that only a flat outside closed end surface 3 of body part 1 is exposed for gripping and withdrawal of the body part 1 from within the cap part 2.

Figure 8:
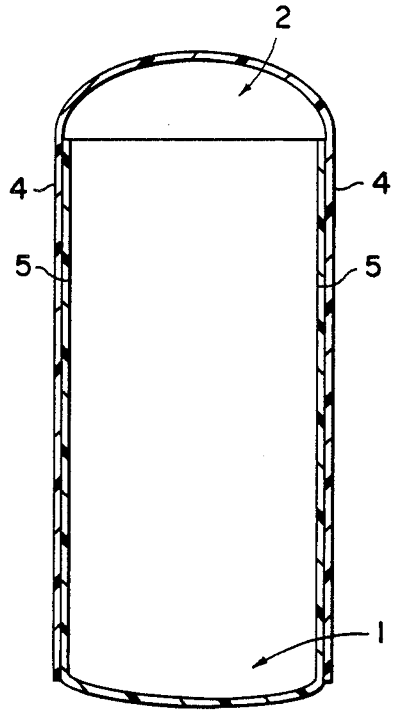

FIG. 8 is a side sectional view of FIG. 7 along line 8—8 showing the continuous and total overlap of cap side wall 4 over the body side wall 5.

Figure 9:
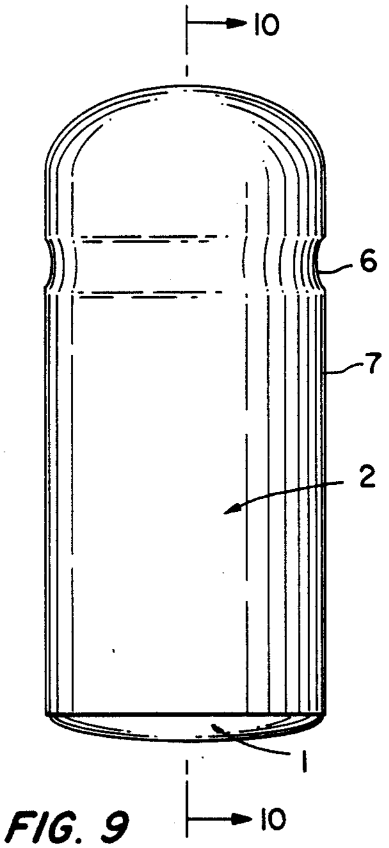

FIG. 9 is a top plan view of a fifth embodiment of the present invention showing the body part 1 telescopically joined within cap part 2, having a locking means of a circumferentially extending ridge 6 extending inwardly from the side wall inner surface 7 of the cap part 2.

Figure 10:
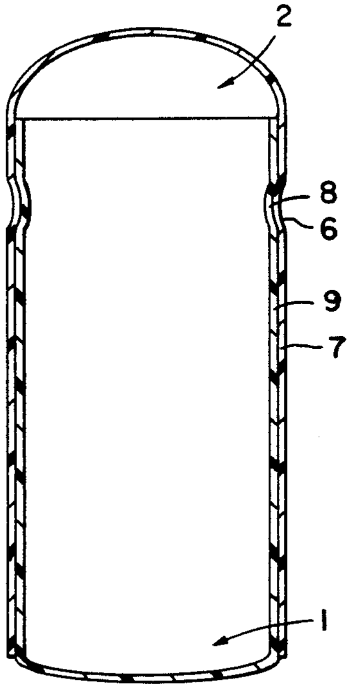

FIG. 10 is a side sectional view of FIG. 9 along line 10—10 showing the locking means of a circumferential extending groove 8 on the side wall outer surface 9 of body part 1 in mating engagement with the circumferentially extending ridge 6 of the inner surface 7 of cap part 2.

Figure 11:
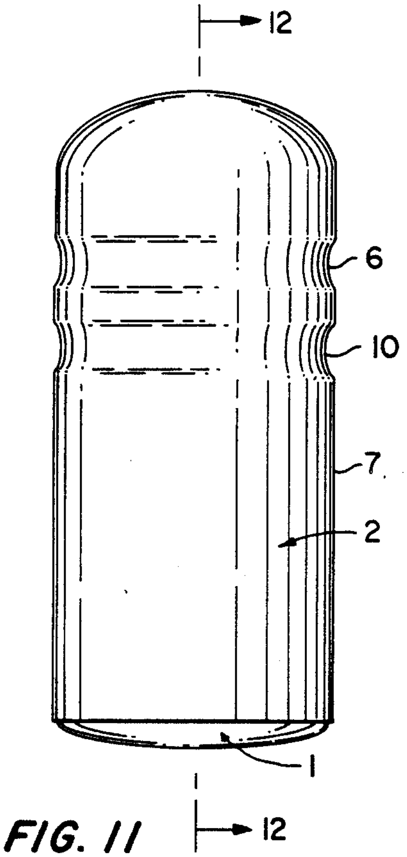

FIG. 11 is a top plan view of a sixth embodiment of the present invention showing the body part 1 telescopically joined within cap part 2 having locking means of two circumferential ridges 6, 10 extending inwardly from the side wall inner surface 7 of cap part 2.

Figure 12:
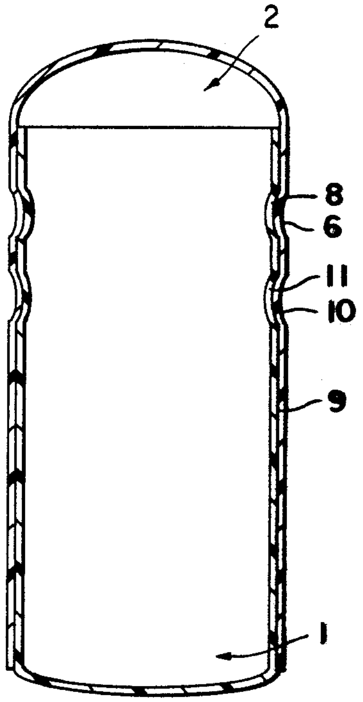

FIG. 12 is a side sectional view of FIG. 11 along line 12—12 showing the locking means of two circumferential grooves 8, 11 extending inwardly from the side wall outer surface 9 of cap part 2 in mating engagement with the ridges 6, 10.

Figure 13:
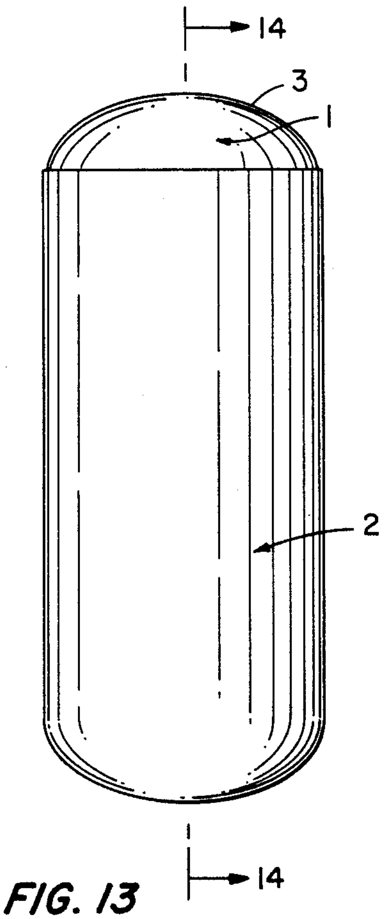

FIG. 13 is a top plan view of a seventh embodiment of the present invention showing the body part 1 telescopically joined within the cap part 2. The body part 1 has a closed end with an outside hemispheroidal surface 3 so that when the parts are joined only the hemispheroidal surface 3 may be gripped with difficulty for separating the body part 1 from from cap part 2.

Figure 14:
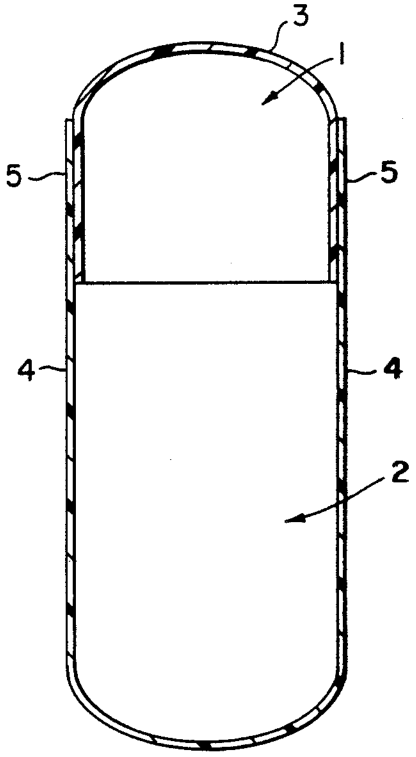

FIG. 14 is a sectional view of FIG. 13 along the line 14—14. The body part 1 has a short side wall 5 which is totally overlapped by the longer side wall 4 of the cap part 2. When the cap part 2 and the body part 1 are telescopically joined, only the closed end outside hemispheroidal surface 3 of body part 1 is exposed for gripping and withdrawal of the body part 1 from within the cap part 2 for the purpose of tampering.

Figure 15:
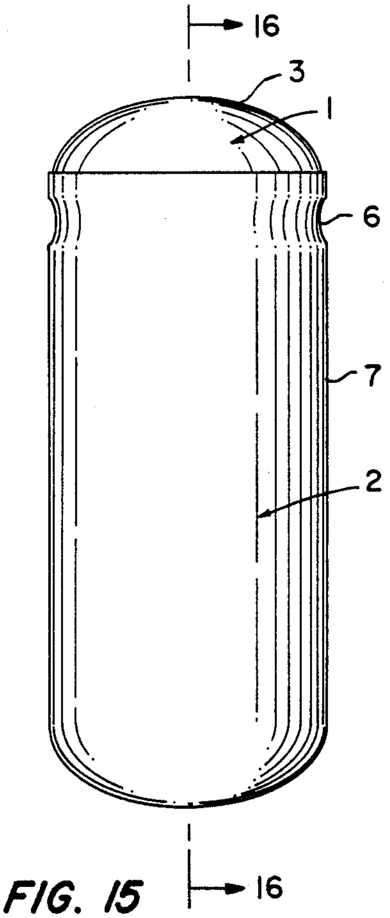

FIG. 15 is a top plan view of an eighth embodiment of the present invention showing the hemispheroidal outside surface closed end 3 of body part 1 enclosed within the cap part 2 having a locking means of a circumferentially extending ridge 6 extending inwardly from the the side wall inner surface 7 of the cap part 2.

Figure 16:
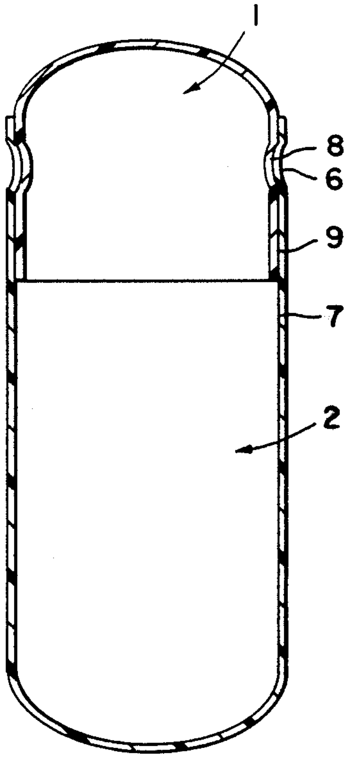

FIG. 16 is a side sectional view of FIG. 15 along line 16—16 showing the locking means of a circumferentially extending groove 8, extending inwardly from the side wall outer surface 9 of body part 1, mating with the circumferentially extending ridge 6 extending inwardly from the side wall inner surface 7 of the cap part 2.

Figure 17:
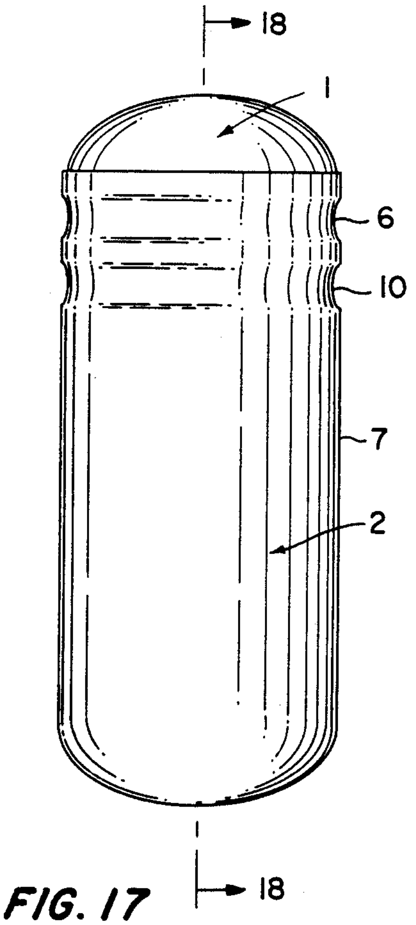

FIG. 17 is a top plan view of a ninth embodiment of the present invention showing the cap part 2 having a locking means of two circumferentially extending ridges 6, 10 extending inwardly from the side wall inner surface 7 of cap part 2.

Figure 18:
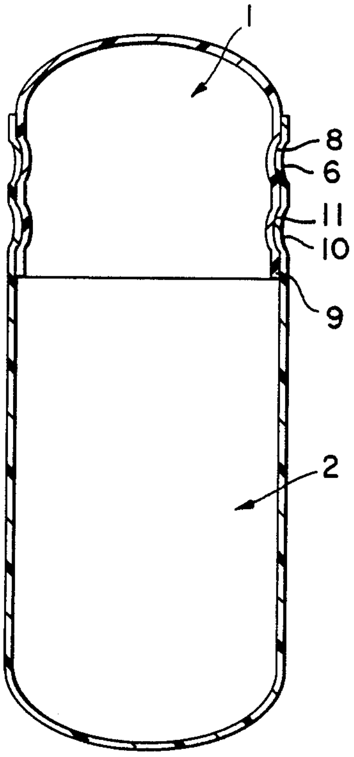

FIG. 18 is a side sectional view of FIG. 17 along line 18—18 showing the body part 1 having locking means of two circumferentially extending grooves, 8, 11 extending inwardly from the side wall outer surface 9 of body part 1, in mating engagement with the ridges 6, 10 of cap part 2.

Figure 19:
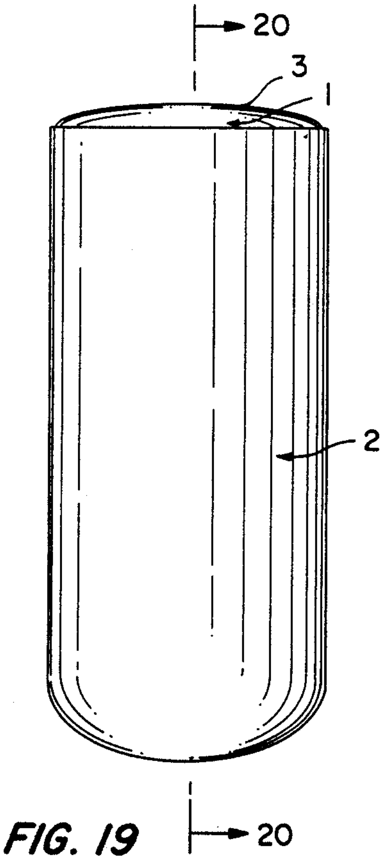

FIG. 19 is a top plan view of a tenth embodiment of the present invention showing a closed end with a flat outside surface 3 or body part 1 telescopically joined within cap part 2.

Figure 20:
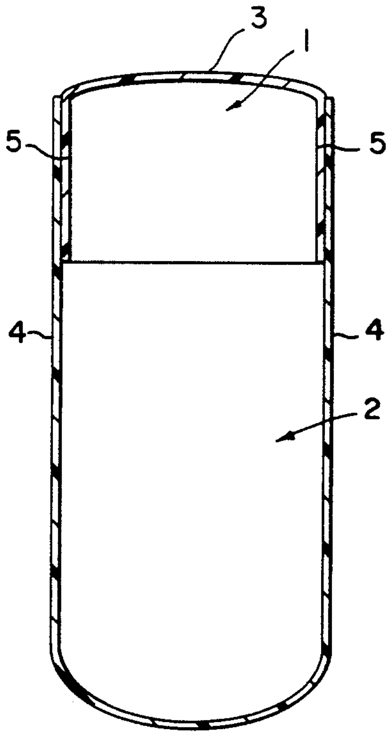

FIG. 20 is a side sectional view of FIG. 19 along line 20—20 showing the side wall 5 of body part 1 completely overlapped by the longer side wall 4 of cap part 2 so that only the flat surface 3 of body part 1 is available for gripping and withdrawal of body part 1 from within cap part 2 for the purpose of tampering.

Figure 21:
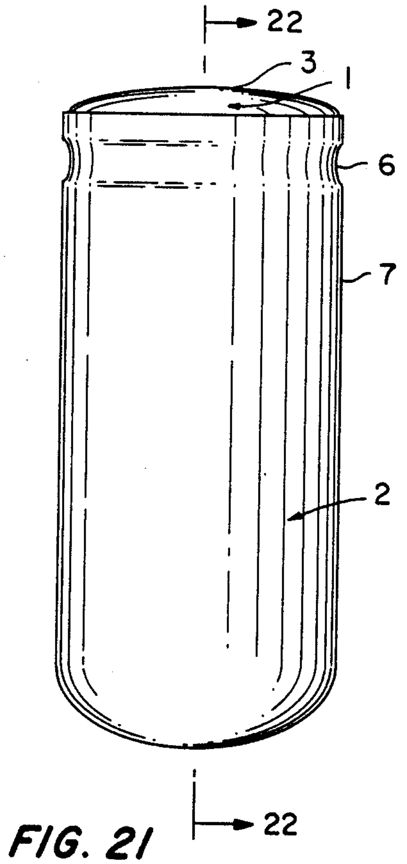

FIG. 21 is a top plan view of an eleventh embodiment of the present invention showing a closed end outside flat surface 3 of body part 1 telescopically joined within cap part 2 having a locking means of a circumferentially extending ridge 6 extending inwardly from the side wall inner surface 7 of cap part 2.

Figure 22:
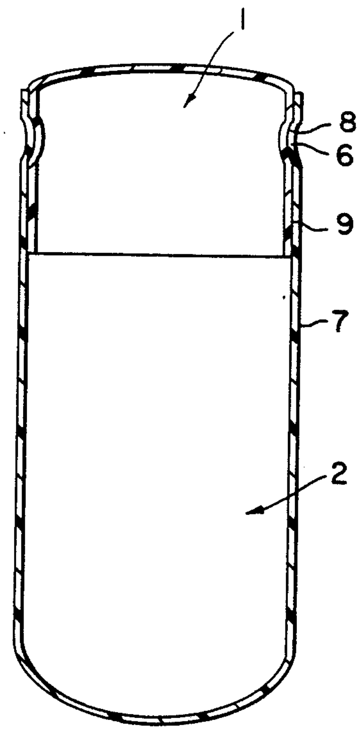

FIG. 22 is a side sectional view of FIG. 21 along line 22—22 showing locking means of the circumferentially extending ridge 6 in mating engagement with a circumferentially extending groove 8 extending inwardly from the side wall outer surface 9 of body part 1 so as to lock the body part 1 within cap part 2 thereby impeding separation and tampering.

Figure 23:
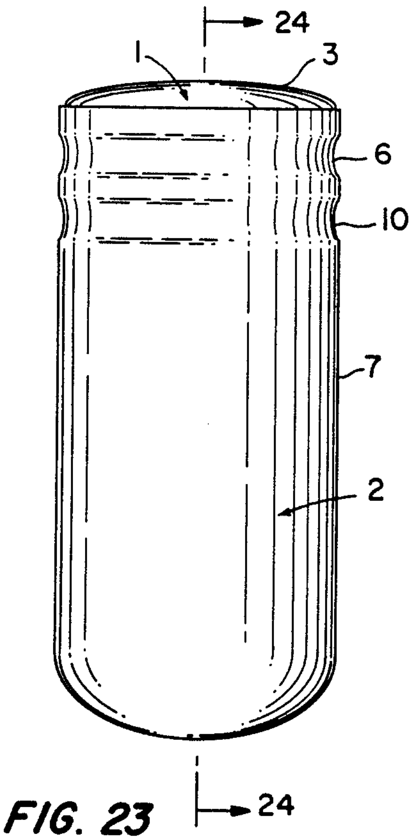

FIG. 23 is a top plan view of a twelfth embodiment of the present invention showing a closed end outside flat surface 3 of body part 1 telescopically joined within cap part 2 having a locking means of two circumferentially extending ridges 6, 10 extending inwardly from the side wall inner surface of 7 of cap part 2.

Figure 24:
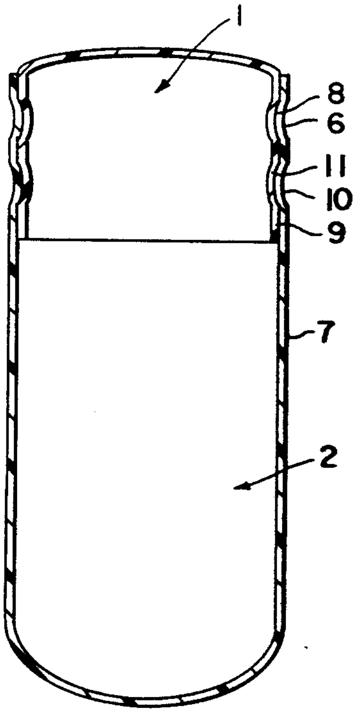

FIG. 24 is side sectional view of FIG. 23 along line 24—24 showing the body part 1 having locking means of two circumferentially extending grooves 8, 11 extending inwardly from the side wall outer surface 9 of the body part 1 in mating engagement with the circumferentially extending ridges 6, 10 of the side wall inner surface 7 of cap part 2 when the capsule parts are joined so as to impede separation and tampering.

Figure 25:
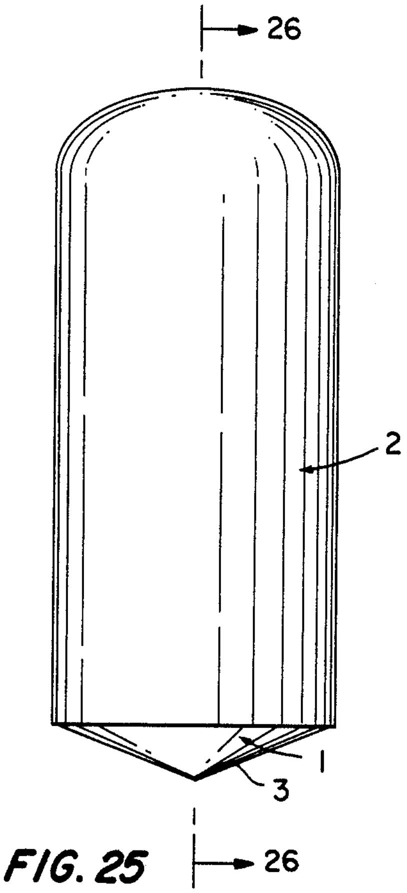

FIG. 25 is a top plan view of a thirteenth embodiment of the present invention showing body part 1 having a closed end with a conical outside surface 3 exposed when the body part 1 is telescopically joined within the cap part 2.

Figure 26:
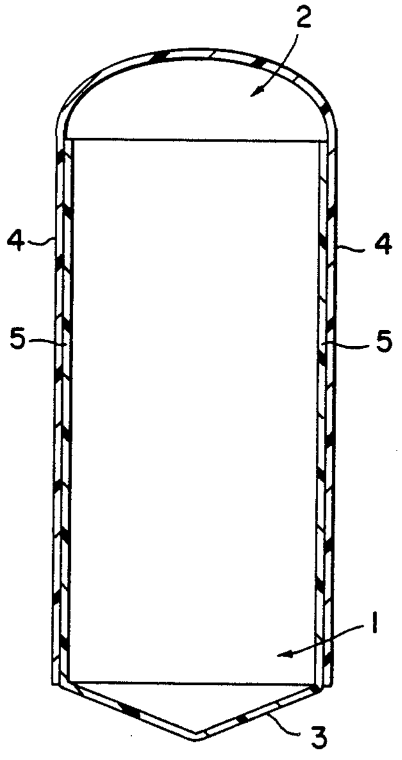

FIG. 26 is a side sectional view of FIG. 25 along line 26—26 showing the side wall 4 of cap part 2 completely overlapping the side wall 5 of body part 1 so that only the conical outside surface 3 of body part 1 is exposed so as to be gripped with difficulty, which impedes separation and tampering.

Figure 27:
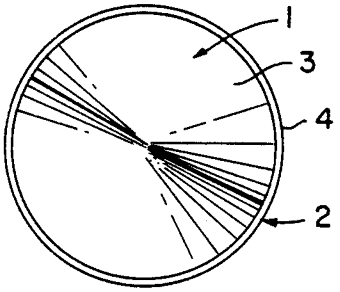

FIG. 27 is a bottom elevational view of FIG. 25 showing the conical outside surface 3 of body part 1 inserted within the side wall 4 of cap part 2.

Figure 28:
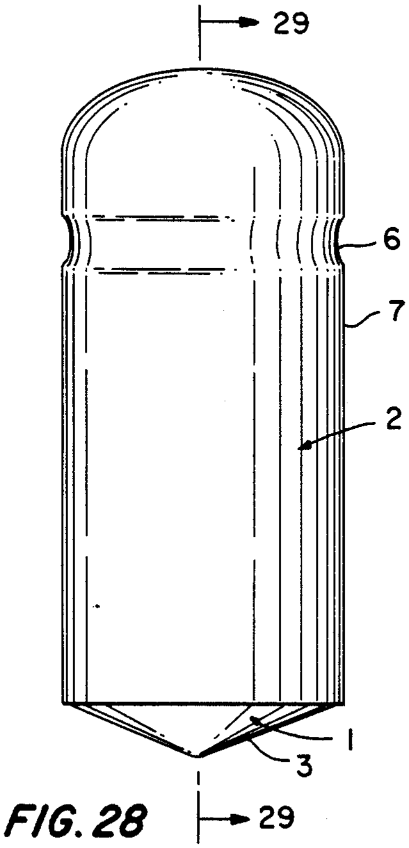

FIG. 28 is a top plan view of a fourteenth embodiment of the present invention showing a closed end outside conical surface 3 of body part 1 which is telescopically joined within cap part 2 having a locking means of a circumferentially extending ridge 6 extending inwardly from the side wall inside surface 7 of cap part 2.

Figure 29:
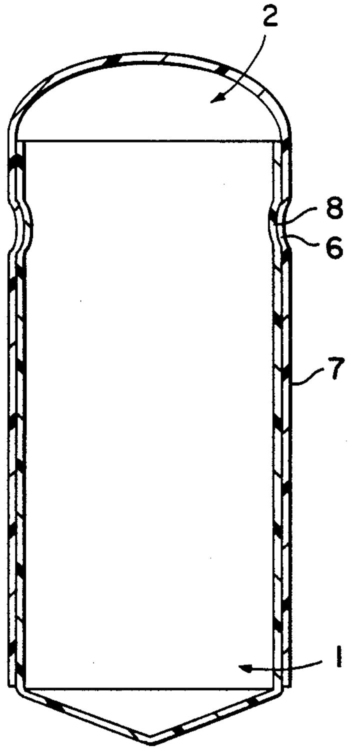

FIG. 29 is a side sectional view of FIG. 28 along line 29—29 showing locking means of a circumferentially extending ridge 6 of the side wall inner surface of the cap part 2 in mating engagement with the circumferentially extending groove 8 on the side wall outer surface 9 of the body part 1 so as to lock the capsule parts 1, 2 and to impede separation and tampering.

Figure 30:
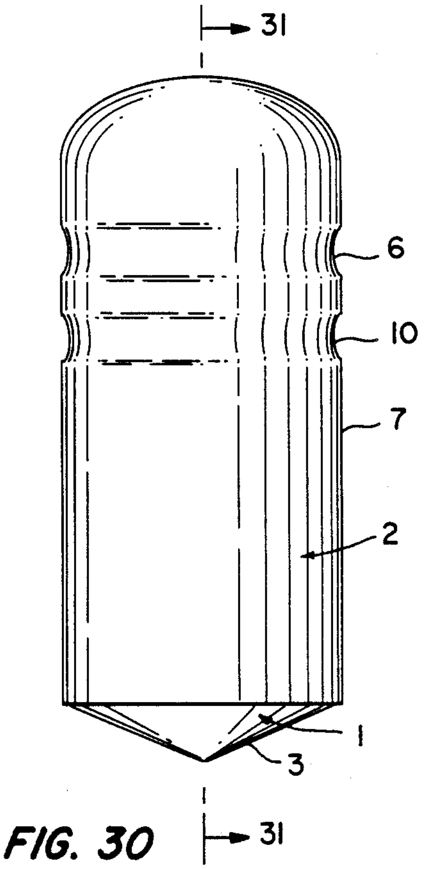

FIG. 30 is a top plan view of a fifteenth embodiment of the present invention showing a body part 1 having a closed outside conical surface 3, the body part 1 being telescopically joined within cap part 2 having a locking means of two circumferentially extending ridges 6, 10 extending inwardly from the side wall inner surface 7 of the cap part 2.

Figure 31:
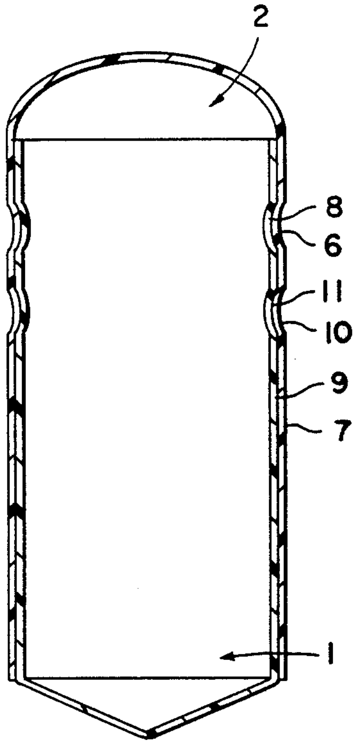

FIG. 31 is a side sectional view of FIG. 30 along line 31—31 showing locking means by the mating of the circumferential ridges 6, 10 of the cap part 2 in engagement with the circumferential grooves 8, 11 extending inwardly from the side wall outer surface 9 of the body part 1 so as to lock the capsule parts 1 and 2 together to impede separating and tampering.

Figure 32:
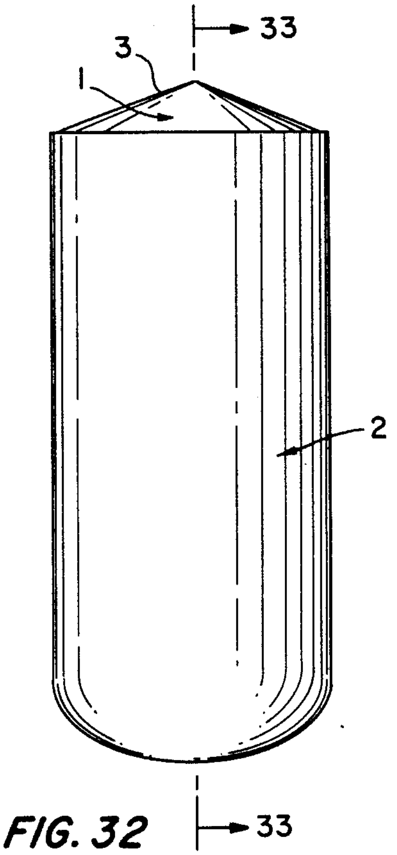

FIG. 32 is a top plan view of a sixteenth embodiment of the present invention showing the body part 1 having a closed end outside conical surface 3, the body part being telescopically joined within the cap part 2.

Figure 33:
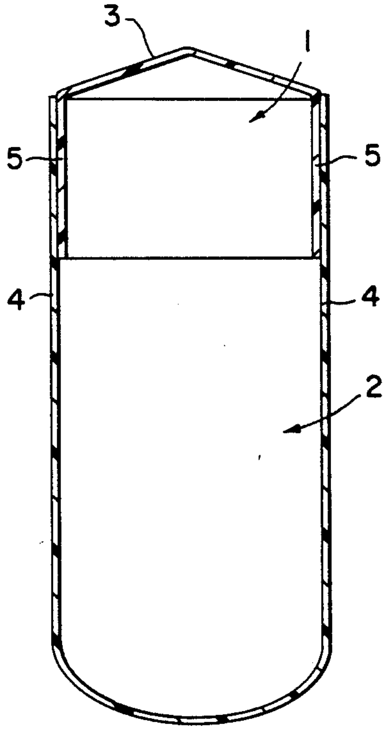

FIG. 33 is a side sectional view of FIG. 32 along line 33—33 showing the body part 1 having a side wall 5 completely overlapped by a longer side wall 4 of cap part 2 so that only the closed end outside conical surface 3 is exposed for gripping when the capsule is telescopically joined, which impedes separating and tampering.

Figure 34:
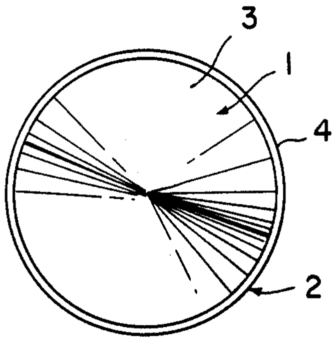

FIG. 34 is a front elevational view of FIG. 32 showing the closed end outside conical surface 3 of body part 1 which is telescopically joined within the side wall 4 of cap part 2.

Figure 35:
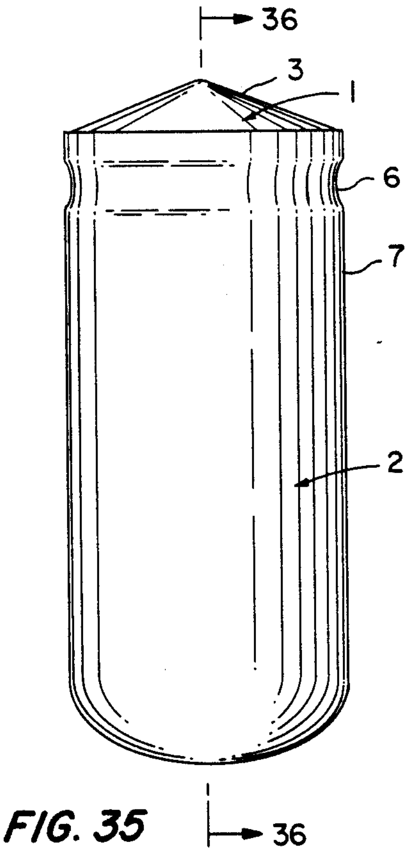

FIG. 35 is a top plan view of a seventeenth embodiment of the present invention showing the body part 1 having a closed end outside conical surface 3, the body part 1 being telescopically joined within cap part 2 having a locking means of a circumferentially extending ridge 6 extending inwardly from the side wall inside surface 7 of cap part 2.

Figure 36:
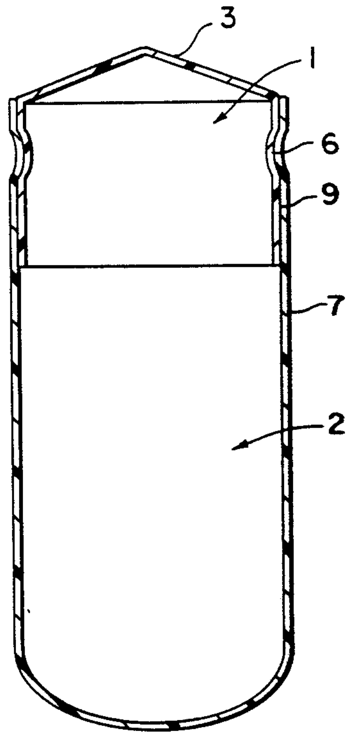

FIG. 36 is a side sectional view of FIG. 35 along line 36—36 showing the locking means of the circumferentially extending ridge 6 in mating engagement with a circumferentially extending groove 8 extending inwardly from the side wall outer surface of side wall 9 of body part 1 which locks the body part 1 within cap part 2 and thereby impedes separation and tampering.

Figure 37:
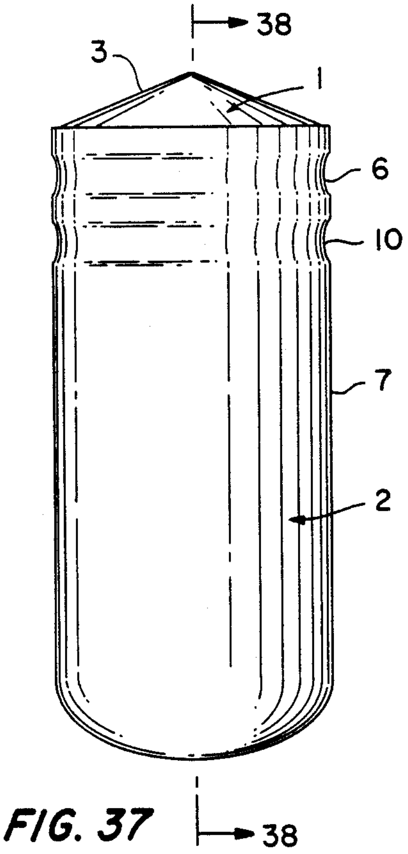

FIG. 37 is a top plan view of an eighteenth embodiment of the present invention showing the body part 1 having a closed end outside conical surface 3 and being telescopically joined within cap part 2 having a locking means of two circumferentially extending ridges 6, 10 extending inwardly from the side wall inner surface 7.

Figure 38:
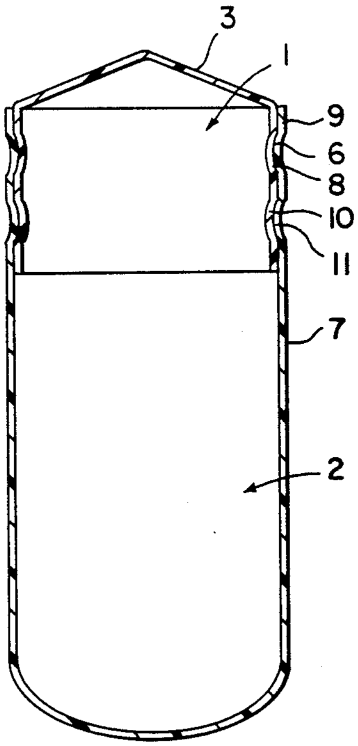

FIG. 38 is a side section view of FIG. 37 along line 38—38 showing the locking means of the two circumferentially extending ridges 6, 10 in mating engagement with two circumferentially extending grooves 8, 11 extending inwardly from the side wall outer surface of body part 1 so as to lock the capsule parts when telescopically joined which impedes separation and tampering.

Figure 39:
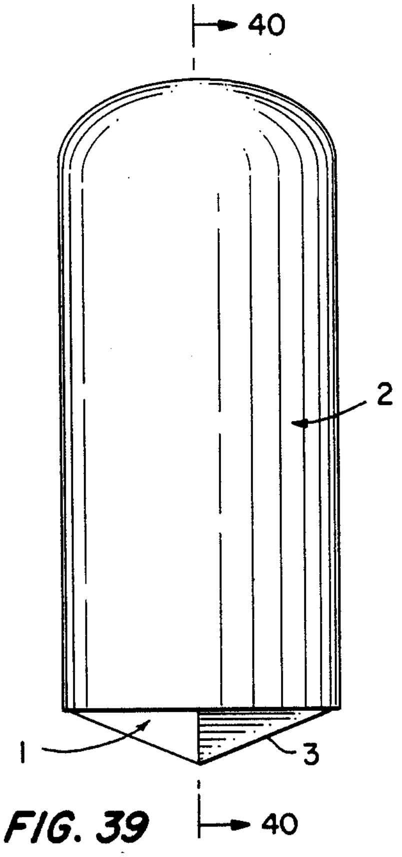

FIG. 39 is a top plan view of a nineteenth embodiment of the present invention showing the body part 1 having a closed end outside pyramidical surface 3 exposed when the body part 1 is telescopically joined within cap part 2.

Figure 40:
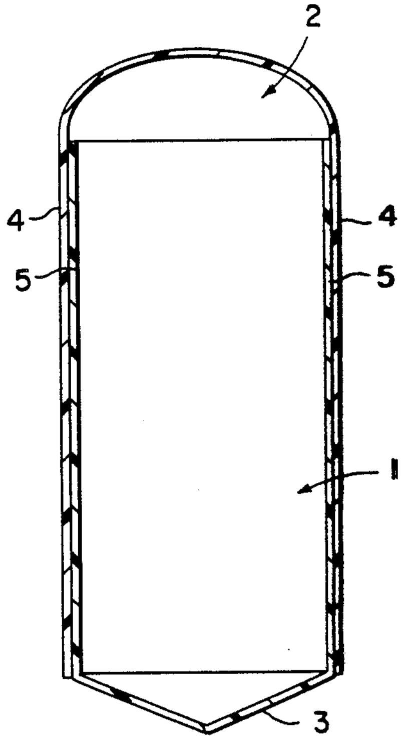

FIG. 40 is a side sectional view of FIG. 39 along line 40—40 showing the side wall 4 of cap part 2 completely overlapping side wall 5 of body part 1 so that only the closed end outside pyramidical surface 3 of the body part 1 can be gripped with difficulty which thereby impedes separation and tampering.

Figure 41:
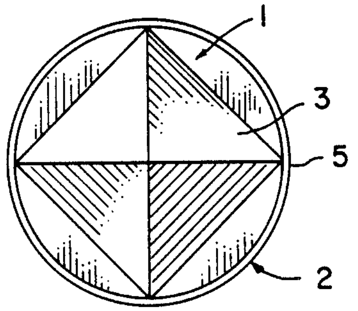

FIG. 41 is a bottom elevational view of FIG. 39 showing the closed end outside pyramidical surface 3 of body part 1 telescopically joined within the side wall 5 of cap part 2.

Figure 42:
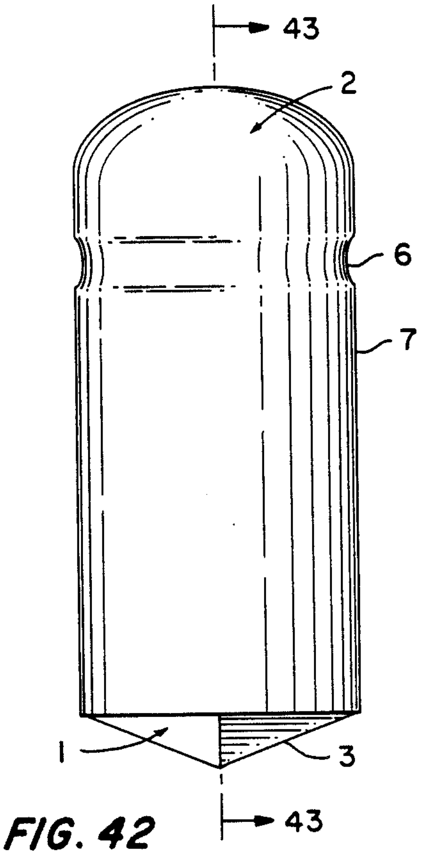

FIG. 42 is a top plan view of a twentieth embodiment of the present invention showing body part 1 having a closed end outisde pyramidical surface 3 and telescopically joined within cap part 2 having a circumferentially extended ridge 6 extending inwardly from the inner surface 7 of cap part 2.

Figure 43:
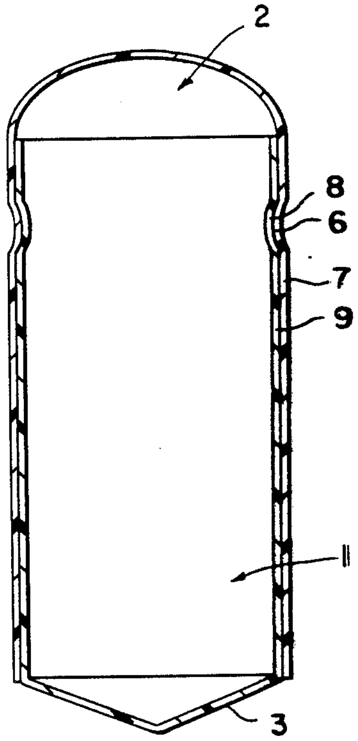

FIG. 43 is a side sectional view of FIG. 42 along line 43—43 showing the body part 1 having circumferentially extending groove 8 on the side wall outside surface 9 in mating in engagement with the ridge 6 of cap part 2 so as to impede separation and tampering with the joined capsule.

Figure 44:
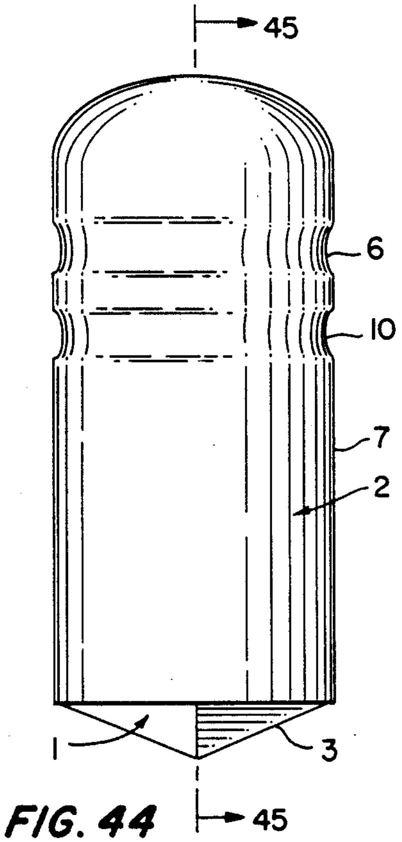

FIG. 44 is a top plan view of a twenty-first embodiment of the present invention showing the body part 1 having a pyramidical outside surface on the closed end 3, and telescopically joined within cap part 2 having two circumferential ridges 6, 10 extending inwardly from the side wall inner surface 7 of the body part 1.

Figure 45:
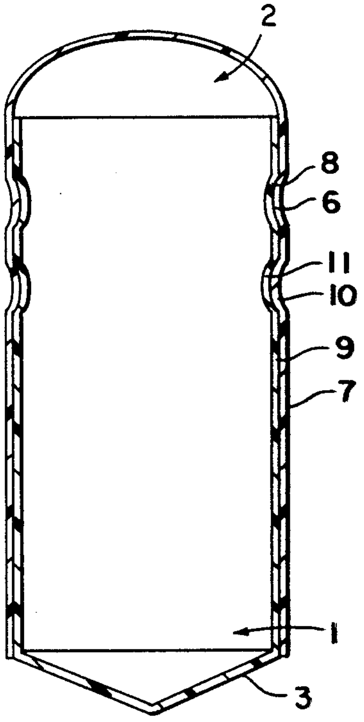

FIG. 45 is a side sectional view of FIG. 44 along line 45—45 showing the circumferential ridges 6, 10 of body part 2 in mating engagement with the circumferential groove 8, 11 extending inwardly from the side wall outer surface of body part 1 so as to impede separation of and tampering with the capsule.

Figure 46:
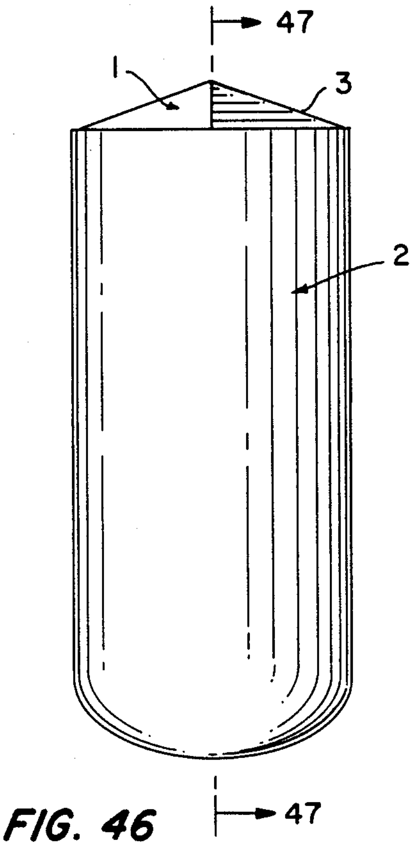

FIG. 46 is a top plan view of a twenty-second embodiment of the present invention showing the body part 1 having a pyramidical outside surface on the closed end 3, and telescopically joined within cap part 2.

Figure 47:
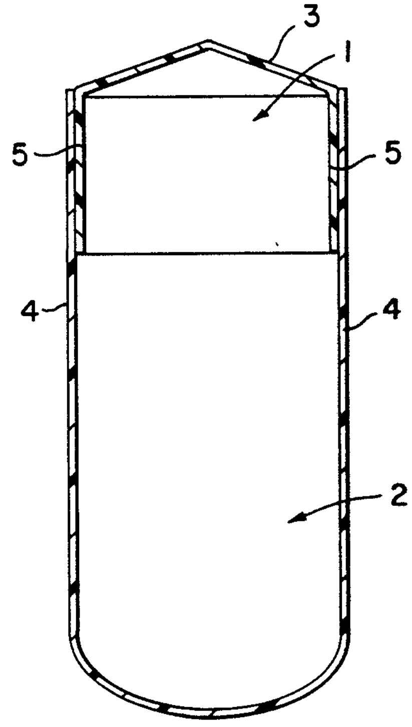

FIG. 47 is a side sectional view of FIG. 46 along line 47—47 showing the body part side wall 5 totally overlapped by the substantially longer cap part side wall 4 so that only the outside closed end pyramidical surface 3 is exposed for gripping which impedes separation of and tampering with the capsule.

Figure 48:
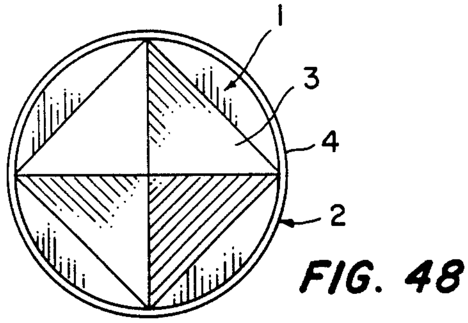

FIG. 48 is a top elevational view of FIG. 46 showing the closed end outside pyramidical surface 3 of body part 1 telescopically joined within the side wall 4 of cap part 2.

Figure 49:
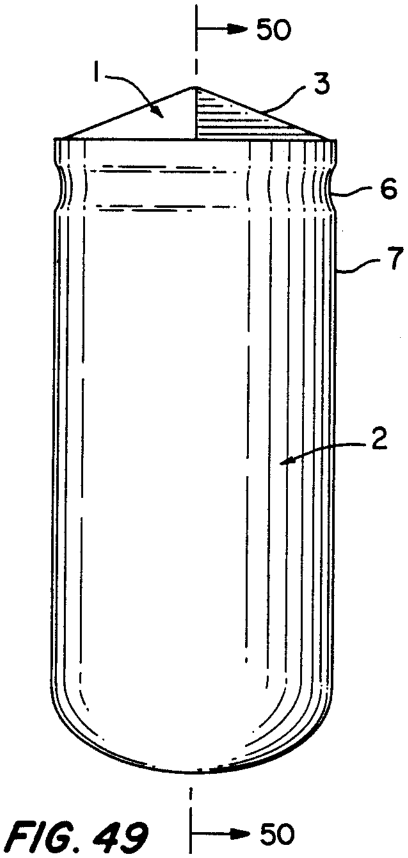

FIG. 49 is a top plan view of a twenty-third embodiment of the present invention showing the body part 1 having a closed end outside pyramidical surface 3, and telescopically joined within cap part 2 having a circumferentially extended ridge 6 extending inwardly from the side wall inner surface 7 of cap part 2.

Figure 50:
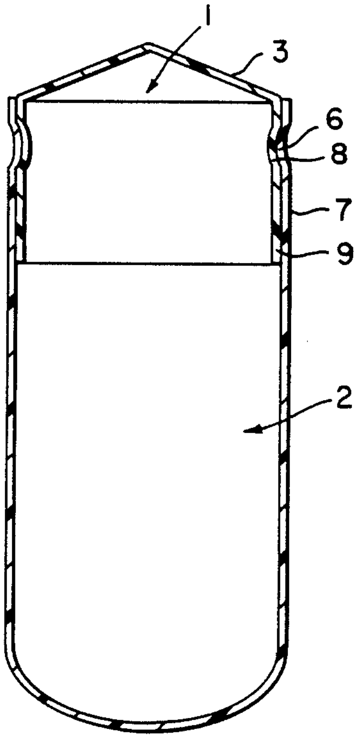

FIG. 50 is a side sectional view of FIG. 49 along line 50—50 showing a circumferential groove 8 extending inwardly from the side wall outer surface 9 of body part 1 and in mating engagement with ridge 6 so as to lock the capsule parts and impede separation of and tampering with the capsule.

Figure 51:
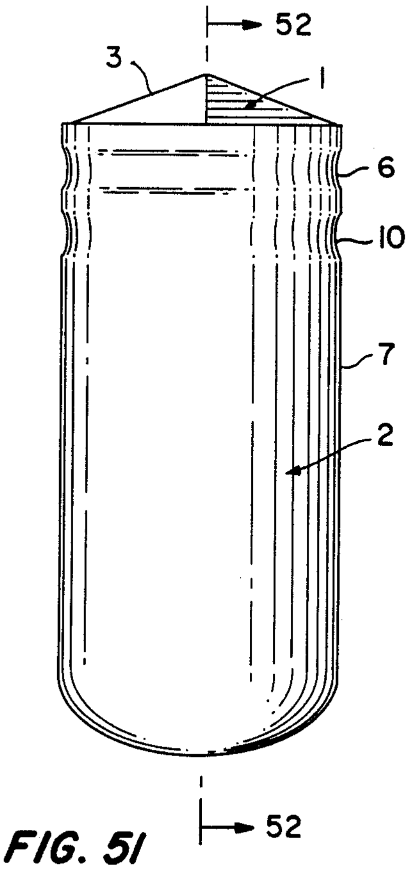

FIG. 51 is a top plan view of a twenty-fourth embodiment of the present invention showing the body part 1 having a closed end outside pyramidical surface 3, and telescopically joined within cap part 2 having circumferentially extending ridges 6, 10 extending inwardly from the side wall inner surface 7 of cap part 2.

Figure 52:
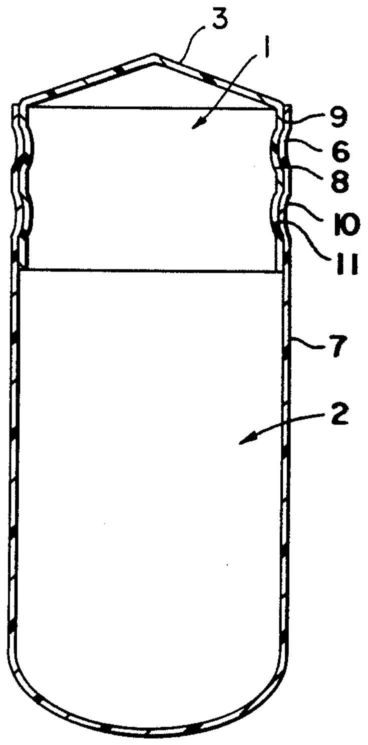

FIG. 52 is a side sectional view of FIG. 51 along line 52—52 showing the body part 1 having circumferential grooves 8, 11 extending inwardly from the side wall outer surface 9 of body part 1 in mating engagement with the ridges 6, 10 so as to lock the capsule parts and impede separation of and tampering with the capsules.

Figure 53:
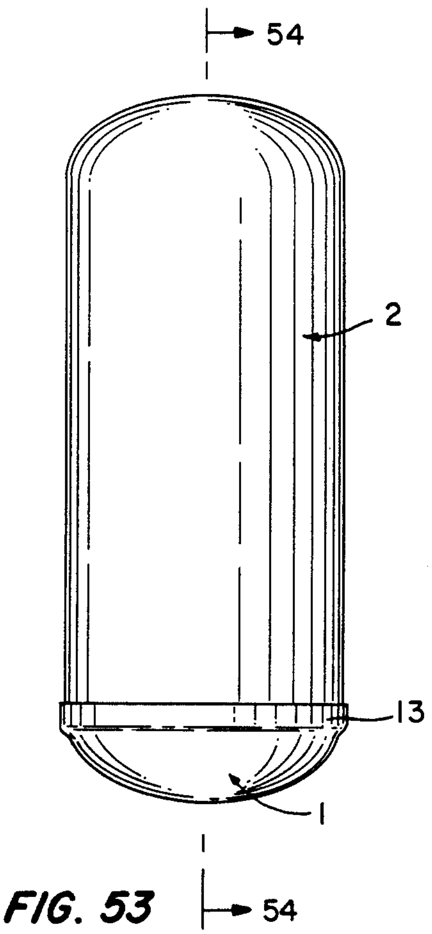

FIG. 53 is a twenty-fifth embodiment of the present invention showing the cap part 2 with a seal 13 enclosing both the open end of the cap part 2 and the closed end of the body part 3 telescoped within the joined capsule.

Figure 54:
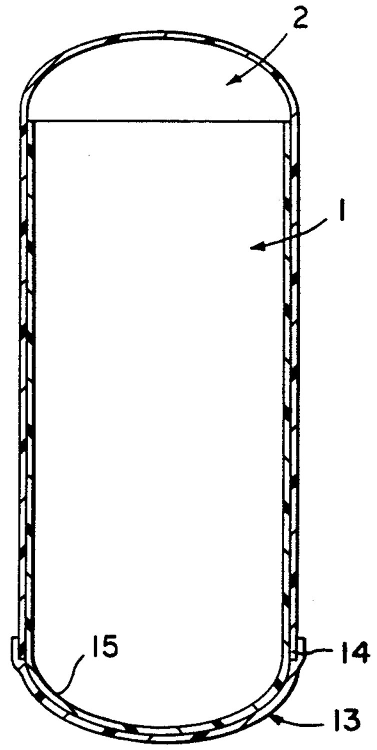

FIG. 54 is a side sectional vie of FIG. 53 along line 54—54 showing the body part 1 telescopically joined within cap part 2. The open end 14 of cap part 2 and the closed end 15 of body part 1 are completely covered with seal 13 so as to further impede separation of and tampering with the joined capsule.

It is to be understood that the seal of this embodiment can be used with any of the embodiments of the present invention as described herein.

Figure 55:
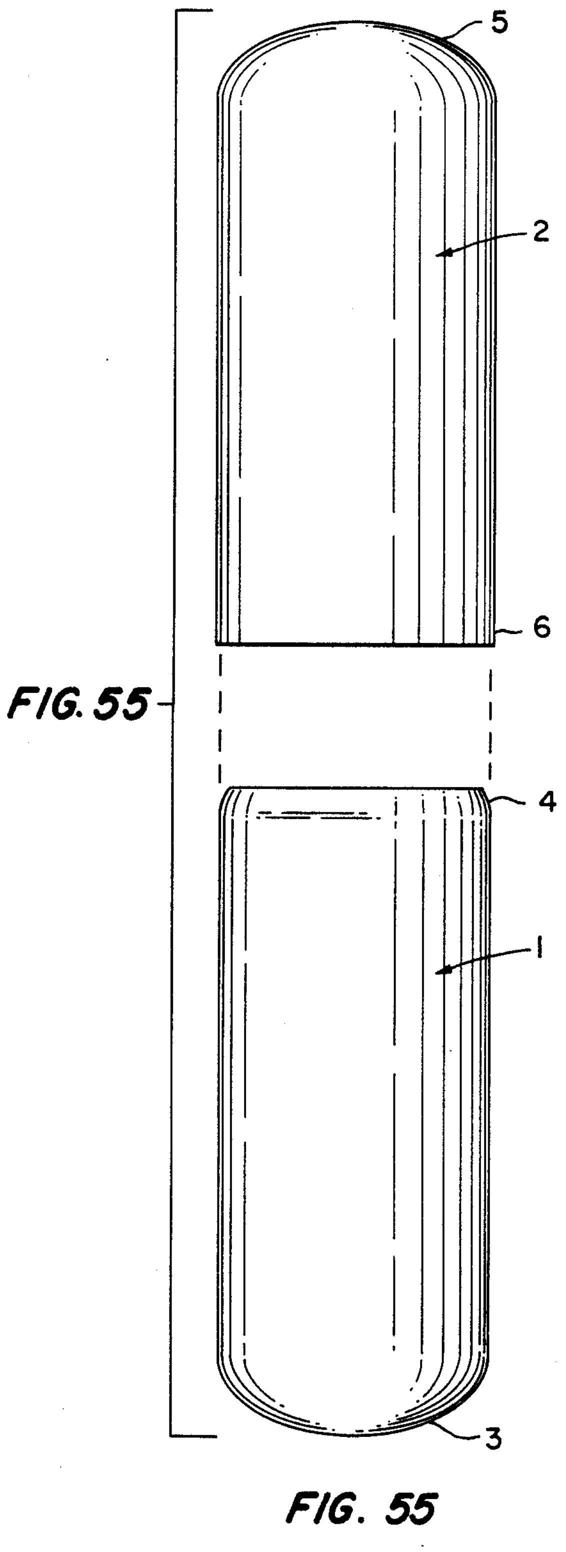

FIG. 55 is a top plan exploded view of a twenty-sixth embodiment of the invention showing a capsule body 1 having substantially the shape of a cylinder closed at one end 3 and having a reduced diameter in the area of its open end 4; and a capsule cap part 2 having substantially the shape of a cylinder closed at one end 5 and having an open end 6 opposite therefrom.

Figure 56:
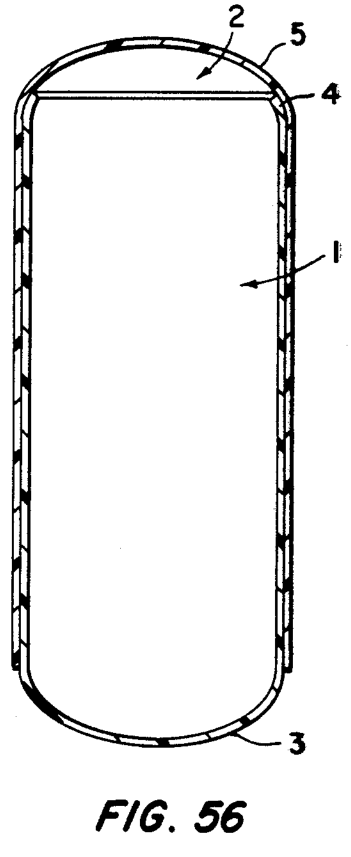

FIG. 56 is a side sectional view of the assembled tamper-proof capsule of FIG. 55 showing the free edge of the reduced diameter of the closed end 4 of the body part 1 has moved freely and smoothly within the open end 6 of cap part 2 so as not to damage the edge of open end 6. When completely joined the reduced diameter of the open end 4 of the body part 1 is in frictional engagement with the closed end 5 of the cap part 2.

It is to be understood that the body part reduced diameter of this embodiment can be used with any of the embodiments of the present invention as described herein.

Figure 57:
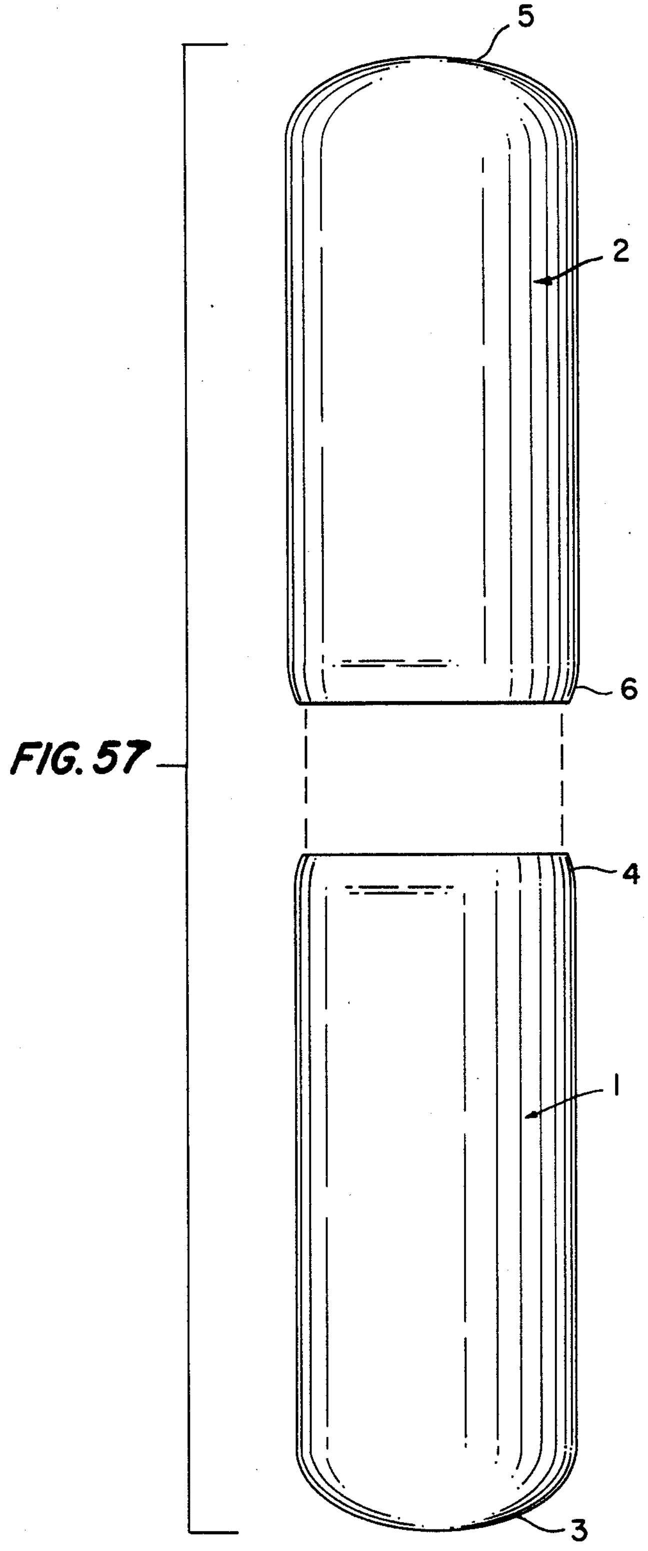

FIG. 57 is a top plan exploded view of a twenty-seventh embodiment of the present invention showing the body part 1 having substantially the shape of a cylinder closed at one end 3 and a reduced diameter in the area of its open end 4; the cap part having substantially the shape of a cylinder closed at one end 5 and having a reduced diameter in the area of its open end 6.

Figure 58:
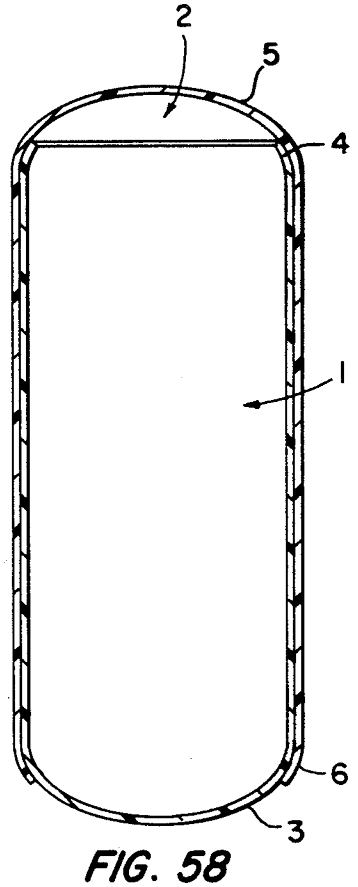

FIG. 58 is a side sectional view of the assembled tamper-proof capsule of FIG. 55 showing the reduced diameter of the open end 4 of capsule body 1 in frictional engagement with the closed end 5 of cap part 2 when telescopically joined; and showing the reduced diameter of the closed end 6 of cap part 6 in frictional engagement with the closed end 3 of cap part 1, which further impedes separation of and tampering with the joined capsule.

It is to be understood that the body part and cap part reduced diameter of this embodiment can also be used with any of the embodiments of the present invention as described herein.

Figure 59:
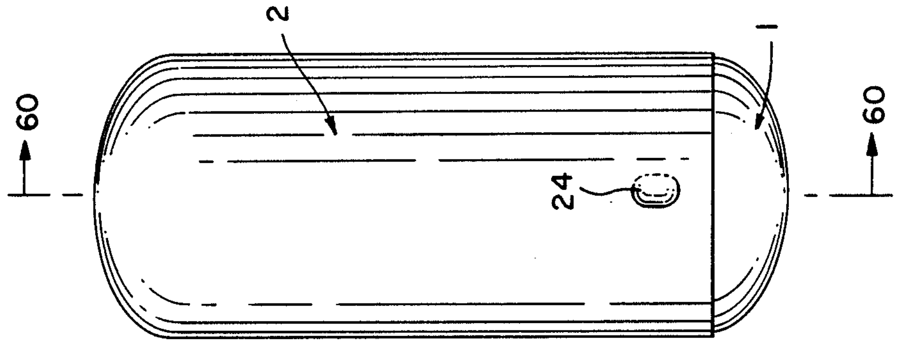

FIG. 59 is a side view of a twenty-eighth embodiment of the invention showing a body part 1 and a cap part 2 having an indent 24.

Figure 60:
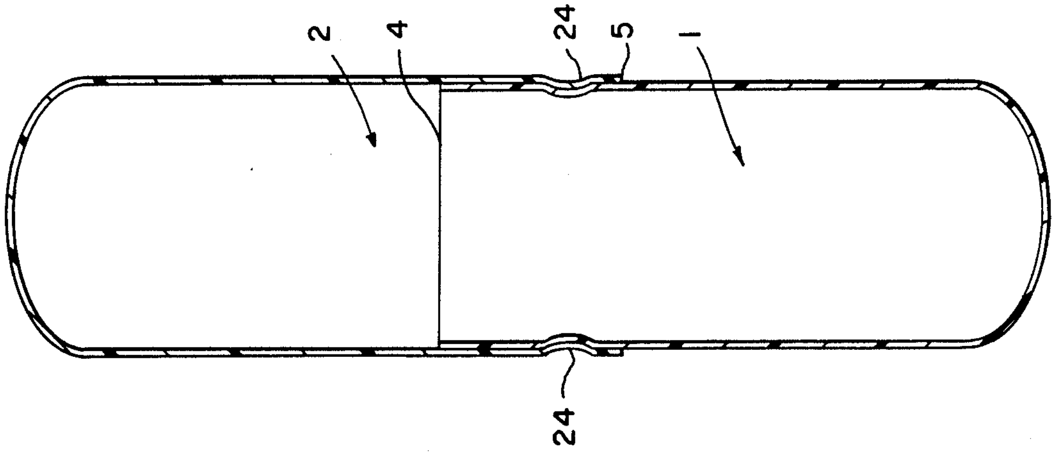

FIG. 60 is a sectional view along line 60—60 of the capsule of the preset invention in a pre-locked or partly closed position. The indent 24 of cap part 2 provides a friction fit wherein the capsule parts are elastically distorted—the cap undergoing "ovalling" and the body "dimpling", making for increased air passage means or air vent means so as to permit the escape of compressed air contained within the capsule caused by the entry of the open end 4 of body part 1 within the open end 5 of the cap part 2.

Figure 61:
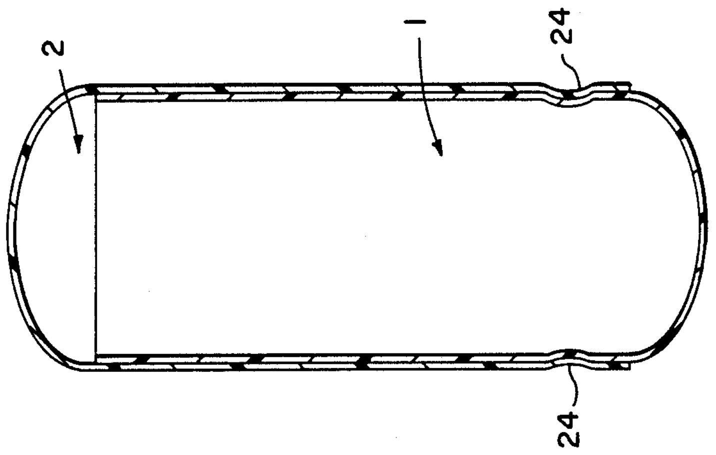

FIG. 61 is a sectional view of the capsule in the fully closed or telescopically joined position showing the ident 24 having acted as a passage or vent which permitted the escape of compressed air contained within the capsule during the completion of telescopic joining.

It is to be understood that the cap part indent of this embodiment can be used as a body part indent and also with any of the embodiments of the present invention as described herein.

All of the enbodiment of the present invention can be produced on capsule-making machines utilizing dip-molding technology. Such technology involves the forming of hard shell gelatin capsules by dipping of capsule-shaped pins into a gelatin solution, removing the pins from the solution, drying of the gelatin upon the pins, stripping off the gelatin capsule parts from the pins, adjusting for length, cutting, joining and ejecting the capsules.

When the term "gelatin" is used in this specification, gelatin and/or other hydrophilic polymer materials whose properties are pharmaceutically acceptable as capsule materials are also included.

In addition to the above embodiments the present invention may also include a sealing of the capsule when the capsule parts are telescopically joined. The sealing of the joined capsule provides an additional securing of the capsule parts which further impedes separation for the purposes of tampering. The sealing of the capsule may be accomplished as follows:

1. Sealing of the capsule by spraying or dipping in polymer solutions or emulsions including:
   a. Polyalkylenes such as polyethylene, polypropylene and the like;
   b. Cellulose, its microcrystalline or microfibrillated form, and derivatives thereof, including cellulose esters such as cellulose acetate, hydroxyprophylmethylcellulose-phthalate, hydroxypropylmethylcellulose, celluloseacetate-phthalate, cellulose ethers such as lower alkyl cellulose, wherein the lower alkyl group contains from 1 to 3 carbon atoms as for example ethyl cellulose, methylcellulose, other derivatives such as sodium-carboxymethyl-cellulose, and lower hydroxy-alkyl-cellulose wherein the lower alkyl has from 1 to 4 carbon atoms;
   c. Waxes such as carnauba wax;
   d. Polyvinylpyrrolidone;
   e. Polymers and copolymers of acrylic acids and methacrylic acids and salts and esters thereof;
   f. Carbohydrates including mono-, di-, and poly saccharides such as glucose, sucrose, starch, agar, polydextrose and the like;
   g. Proteins such as gelatin and hydrolyzed gelatin, with derivatives thereof, soy bean proteins, sunflower proteins, and the like;
   h. Shellac;
   i. Rubber;
   j. Polyvinyl-acetates;
   k. Polyuronic acids like alginates and its derivatives; and
   l. Related materials and combinations of the The concentrations of the polymer solutions or emulsions may vary widely and are preferably used as follows:

For dipping 2–50% by weight

For spraying 2–70% by weight

2. In addition to the polymer solutions or emulsions listed under 1, above, the following softeners may also be used:
   a. Poly-hydroxy-alcohols like glycerol, sorbitol, mannitol, and the like;
   b. Dialkylphthalates preferably where alkyl is butyl;
   c. Lower alkyl citrates wherein lower alkyl has 1–6 carbon atoms;
   d. Polyglycols such as polyethyleneglycol and methoxy-propylene-glycol, and 1,2-propyleneglycol;
   e. Esters of polyhydroxy-alcohols such as mono-, di-and tri-acetate of glycerol and the like;
   f. Reocineoleic acid and esters thereof, and long chain fatty acids and esters thereof;
   g. related materials and mixtures of the above.

The above softeners are used in a concentration range of 0.1–20% by weight based on the polymer solutions or emulsions listed under 1 above.

3. In addition to the polymers and the softeners listed under 1 and 2 above any solvent may also be used that is non-toxic for pharmaceutical capsules and is compatible with the capsule composition. Examples of such solvents include:

a. Organic Solvents such as
   (1) Lower alkyl ethers wherein lower alkyl has 1–4 carbon atoms;
   (2) Lower alkyl ketones wherein lower alkyl has 1–8 carbon atoms;
   (3) Methyleneglycol;
   (4) Lower alkyl esters of lower alkyl carboxylic acids wherein the lower alkyl has more than 1–4 carbon atoms; and
   (5) Related materials of the above and lower alkyl alcohols such as ethanol and isopropanol.

b. Water; and c. Related materials and combinations of the above.

4. Various techniques may be used for sealing the capsule. The preferred techniques involve spraying and dipping. These methods are described below:

a. Spraying—The spraying of the body closed end and cap open end of a filled capsule so as to completely seal the seam therebetween is performed with a solution of the polymers indicated under 1 in organic solvents or an emulsion of these polymers in an aqueous medium at a concentration of 50–60% by weight and at a temperature of 50°–80° C. so that the solvent completely evaporates rapidly during the process.

b. Dipping—The dipping of the body closed end of a filled capsule so as to completely seal the seam between the body closed end and the cap is performed by dipping in a solution or emulsion of the polymers indicated under 1 in the solvents indicated under 3 at a concentration of 2–50% by weight and at a temperature range between 20°–50° C.

The present invention is further illustrated by the following examples. All parts and percentages in the examples as well as in the specification and claims are by weight unless otherwise specified.

EXAMPLE 1

10 grams of shellac and 1 gram of glycerol are dissolved in 100 grams of isopropanol at 80° C. and the solution is cooled to 45° C.

The body closed end of a filled hard gelatin capsule is then dipped into the solution at 45° C. for 5; seconds so as to completely seal the seam between the body closed end and the cap. The capsule is then dried for 10 minutes at 30° C. and 30% relative humidity in a drying chamber with air circulation.

EXAMPLE 2

10 grams of shellac and 1 gram of glycerol are combined with 100 grams of water at 70° C. and mixed for 15 minutes with a mixer in order to obtain a homogeneous emulsion. The capsule is dipped as described in Example 1 for 3 seconds into the emulsion at 55° C. and then dried for 10 minutes at 30° C. and 30% relative humidity in a drying chamber with air circulation.

EXAMPLE 3

3 grams of cellulose-acetate-phthalate, 1 gram of diethylacetatephthalate and 1 gram of silicon oil are dissolved in 30 grams of ethylacetate and 65 grams of acetone at 35° C. The body closed end of a filled hard gelatin capsule is then dipped into this solution at 35° C. so as to completely seal the seam between the body closed end and the cap. The capsules are dried for 10 minutes at 30° C. and 30% relative humidity in a drying chamber with air circulation.

EXAMPLE 4

10 grams of shellac and 1 gram of glycerol are dissolved in 100 grams of isopropanol and the solution is kept at 60° C. The body closed .end of a filled hard gelatin capsule is then sprayed with this solution so as to completely seal the seam between the body closed end and the cap. The capsules are dried for 10 minutes at 30° C. and 30% relative humidity in a drying chamber with air circulation.

EXAMPLE 5

30 grams of gelatin is dissolved in 100 grams of water at 80° C. for 1 hour and the solution is allowed to cool to 50° C. The body closed end of a filled hard gelatin capsule is then dipped into this solution for 5 seconds so as to completely seal the seam between the body closed end and the cap. The capsule is dried for 20 minutes at 30° C. and 30% relative humidity in a drying chamber with air circulation.

EXAMPLE 6

6 micrograms of a solution of 55% by weight of hydrolized animal protein (PEPTIDE 2000) in water was applied to the outer surface of a hard gelatin capsule body by a spraying device. After placing the cap part over the body part and waiting for 30 minutes the capsule was completely sealed.

In lieu of sealing the capsule by dipping and spraying, the capsule may be sealed by the application of steam as follows:

Site of Application

A. Between the seam of the cap open end and the body closed end of filled and joined capsules; or B. Inside the cap side wall before joining the filled capsules; or C. Outside the body open end before joining the filled capsules.

Steam

Material

Steam from water having a pH between 1 and 13; or
Water steam combined with glycerol or sorbitol within a range of 5–95%.

Apparatus

Steam jetting device (nozzle).

Conditions

Steam pressure 2.5 kilo/$cm^2$.
Steam quality: 0.8–0.9 saturated.
Nozzle size: 0.25 mm inner diameter.
Distance nozzle/capsule: 2 mm.
Exposure time to steam jet: 0.5–1 second.

Explanation

Sealing is possible at several points or continuously around the capsule circumference.

Rectification on the sealing device is not mandatory for the capsule as the seal lies in the middle of the capsule length.

EXAMPLE 7

Water steam at a saturation of 0.8 is applied with a nozzle having an inner diameter of 0.25 mm at a pressure of 2.5 kilo/$cm^2$ at a distance of 2 mm to the closed body end of a filled hard gelatin capsule for 1 second so as to completely seal the seam between the body closed end and the cap. The capsule is dried for 10 minutes at 30° C. and 30% RH in a drying chamber with air circulation.

In lieu of sealing by steam, the sealing of capsule seam may be accomplished by hot water:

Material

Hot Water having a pH between 1 and 13.

Conditions

Temperature of water: 60°-100° C.
Quantity per capsule: 2-10 microliters.
Distance nozzle capsule: 2 mm
Nozzle size: 0.25 mm.

Site of Application:

Inner surface of capsule cap part before closing the filled capsule; or

Outer surface of capsule body part at groove or ridge site before closing the filled capsule; or Cap end edge of the filled and closed capsule.

Apparatus

Water jetting device (nozzle).

A modified ink jetting device is best used for this purpose.

EXAMPLE 8

5 micrograms of water at a pH of 2.0 and at a temperature of at 80° C. was jetted through a nozzle at a distance of 2 mm on the outer surface of a hard gelatin capsule body part at the site of the groove within a time of 0.5 seconds. After placing the cap part over the body and waiting for 10 seconds the capsule was completely sealed.

While there have been described and illustrated several embodiments of the present invention, the scope and working range of he invention shall not be limited by examples given above. The invention comprises as well various changes and modifications which will occur to those skilled in the art.

It is intended in the appended claims to cover all such changes and modifications as fall within the true spirit and scope of the present invention.

What is claimed is:

1. A hard shell capsule comprising cylindrical, telescopically and frictionally joinable, co-axial cap and body parts, each of said parts having a side wall, an open end and a closed end, wherein the side wall of each of said parts has substantially the same length and said side wall length is substantially greater than said capsule diameter, the closed end of said body part being shaped to resist gripping and, when telescopically joined, the side all of said cap part encases the entire side wall of said body part forming a tamper-proof capsule, whereby the side wall of said body part is prevented from being griped.

2. The hard shell capsule according to claim 1, wherein the closed end of each of said parts has a hemispherical shape.

3. The hard shell capsule according to claim 1, wherein said body part has a reduced sidewall diameter at the open end.

4. The hard shell capsule according to claim 3, wherein said cap part has a reduced side wall diameter at the open end and wherein said capsule body part diameter at its open end is reduced so as to avoid an abutment when the capsule body is telescoped within the capsule cap.

* * * * *